United States Patent [19]

Kost et al.

[11] Patent Number: 4,767,402
[45] Date of Patent: Aug. 30, 1988

[54] ULTRASOUND ENHANCEMENT OF TRANSDERMAL DRUG DELIVERY

[75] Inventors: Joseph Kost, Omer; Drora Levy, Herzlia, both of Israel; Robert S. Langer, Somerville, Mass.

[73] Assignee: Massachusetts Institute of Technology, Cambridge, Mass.

[21] Appl. No.: 883,111

[22] Filed: Jul. 8, 1986

[51] Int. Cl.[4] .............................................. A61B 17/20
[52] U.S. Cl. ........................................ 604/22; 604/20; 604/49; 604/66; 604/290
[58] Field of Search ................. 604/22, 890, 891, 896, 604/897, 306, 49, 93, 28, 289, 290, 304, 66; 128/24 A, 328, 804

[56] References Cited

U.S. PATENT DOCUMENTS

| | | | |
|---|---|---|---|
| 4,127,125 | 11/1978 | Takemoto et al. | 604/22 |
| 4,176,664 | 12/1979 | Kalish | 604/290 |
| 4,280,494 | 7/1981 | Cosgrove, Jr. et al. | 604/66 |
| 4,309,989 | 1/1982 | Fahim . | |
| 4,372,296 | 2/1983 | Fahim | 128/24 A |
| 4,563,184 | 1/1986 | Korol | 604/368 |

FOREIGN PATENT DOCUMENTS

| | | | |
|---|---|---|---|
| 0445433 | 3/1973 | U.S.S.R. | 128/24 A |
| 0556805 | 5/1977 | U.S.S.R. | 604/22 |
| 0591186 | 2/1978 | U.S.S.R. | 604/22 |
| 0506421 | 3/1978 | U.S.S.R. | 604/22 |
| 0910157 | 3/1982 | U.S.S.R. | 128/24 A |

OTHER PUBLICATIONS

D. M. Skauen and G. M. Zentner, "Phonophoresis", Int. J. Pharm. 20, 235–245, (1984).

*Primary Examiner*—C. Fred Rosenbaum
*Assistant Examiner*—Mario Costantino
*Attorney, Agent, or Firm*—Patrea L. Pabst

[57] ABSTRACT

The present invention is a method using ultrasound to enhance permeation of molecules through the skin and into the blood stream, at a controlled rate. Depending on the drug being infused through the skin, the rate of permeation is increased as well as the efficiency of transfer. Drugs which may not be effective under other conditions, for example, due to degradation within the gastrointestinal tract, can be effectively conveyed transdermally into the circulatory system by means of ultrasound.

12 Claims, 5 Drawing Sheets

RELATIVE DRUG PERMEATION IN RATS (in vivo)

TIME (HOURS) FOLLOWING TOPICAL APPLICATION

ULTRASOUND ENHANCEMENT OF TRANSDERMAL DRUG DELIVERY

BACKGROUND OF THE INVENTION

The United Stated Government has certain rights in this invention by virtue of National Institute of Health Grant No. NIH-2R04-GM26698-07.

This invention is generally in the field of drug delivery and more particularly in the area of ultrasound enhanced and controlled transdermal drug delivery.

Drugs are routinely administered either orally or by injection. The effectiveness of most drugs relies on achieving a certain concentration in the bloodstream. Although some drugs have inherent side effects which cannot be eliminated in any dosage form, many drugs exhibit undesirable behaviors that are specifically related to a particular route of administration. For example, drugs may be degraded in the GI tract by the low gastric pH, local enzymes or interaction with food or drink within the stomach. The drug or disease itself may forestall or compromise drug absorption because of vomiting or diarrhea. If a drug entity survives its trip through the GI tract, it may face rapid metabolism to pharmacologically inactive forms by the liver, the first-pass effect. Sometimes the drug itself has inherent undesirable attributes such as a short half-life, high potency or a narrow therapeutic blood level range.

Recently, efforts aimed at eliminating some of the problems of traditional dosage forms involve transdermal delivery of the drugs. Topical application has been used for a very long time, mostly in the treatment of localized skin diseases. Local treatment, however, only requires that the drug permeate the outer layers of the skin to treat the diseased state, with little or no systemic accumulation. Transdermal delivery systems are specifically designed to obtain systemic blood levels. Transdermal permeation or percutaneous absorption can be defined as the passage of a substance, such as a drug, from the outside of the skin through its various layers into the bloodstream.

The transport of drugs through the skin is complex since many factors influence their permeation. These include the skin structure and its properties, the penetrating molecule and its physical-chemical relationship to the skin and the delivery matrix, and the combination of the skin, the penetrant, and the delivery system as a whole. Topical application of drugs has focused much attention on skin permeability properties. Many reports have described efforts to change skin permeability using chemical enhancers, molecules which enter the stratum corneum and decrease its resistance to drug penetration, or by external means such as iontophoresis. Chemical agents such as dimethylsulfoxide (DMSO), or 1-dodecylazacycloheptan-2-one (Azone), tend to enhance the penetration of drugs that are incorporated within them. However, in all of these systems, with the exception of iontophoresis, there is no way of externally controlling the rate of drug release.

U.S. Pat. No. 4,309,989 to Fahim discloses the topical application of a medication using ultrasound with a coupling agent such as oil. Ultrasound at a frequency of at least 1000 kHz and a power of one to three $W/cm^2$ was used to cause selective localized intracellular concentration of a zinc containing compound for the treatment of herpes simplex virus. An important limitation of the disclosed method is that it applies only to topical application and intracellular localization of the drug.

Figure 1:
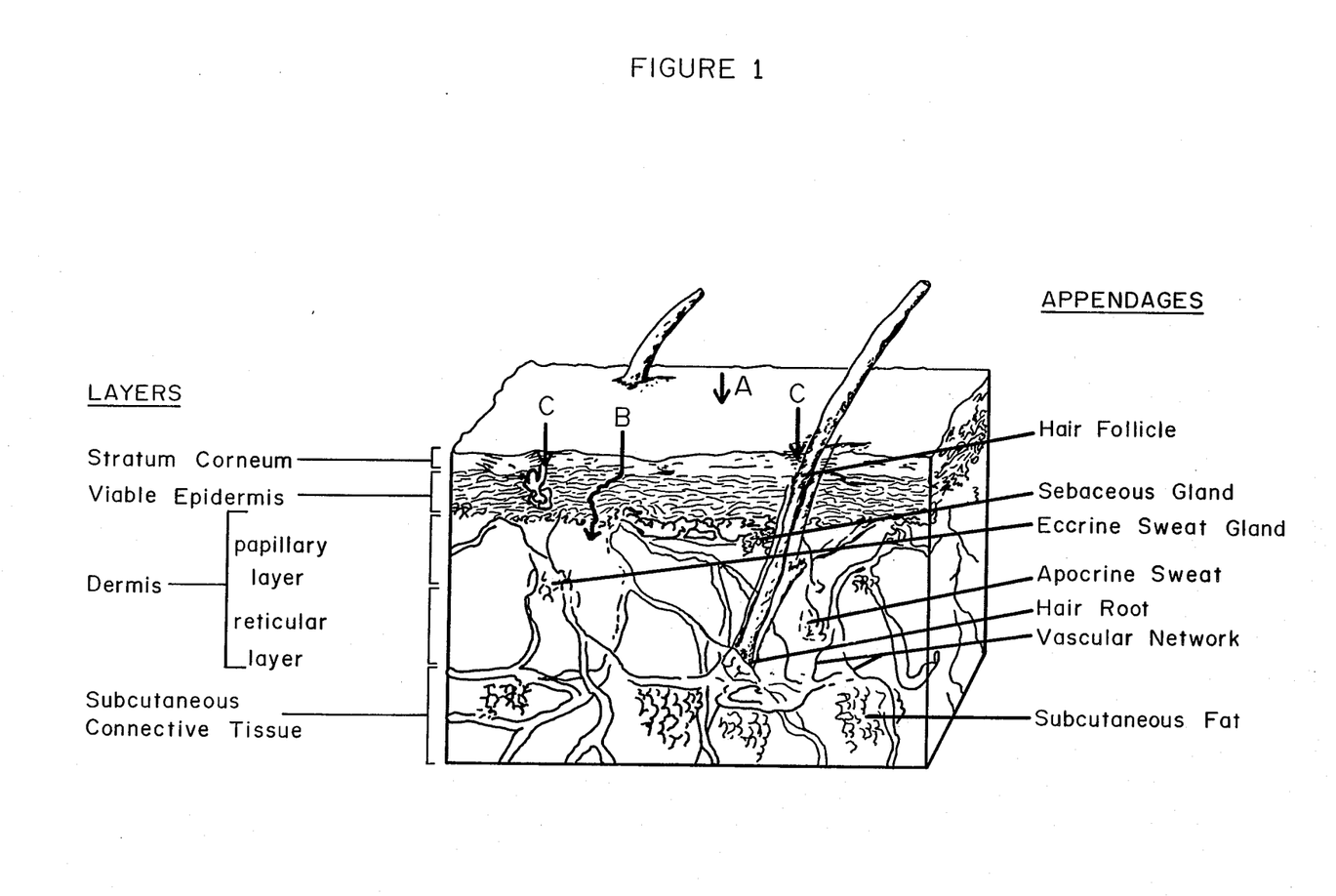
FIG. 1 is a cross-sectional view of human skin.

As shown in FIG. 1, the skin is a complex structure. There are at least four distinct layers of tissue: the non-viable epidermis (stratum corneum), the viable epidermis, the viable dermis (corium), and the subcutaneous connective tissue (hypodermis). Located within these layers are the skin's circulatory system, the arterial plexus, and appendages, including hair follicles, sebaceous glands and sweat glands. The circulatory system lies in the dermis and tissues below the dermis. Diffusion mechanisms provide for the exchange of nutrients between the epidermis and the blood. The capillaries do not actually enter the epidermal structure but come within 150 to 200 microns of the outer surface of the skin.

As shown in FIG. 1, permeation of the skin can occur by (a) transcellular penetration, through the stratum corneum; (b) intercellular penetration, through the stratum corneum; and (c) transappendageal penetration, especially including the sebaceous pathway of the pilosebaceous apparatus and the aqueous pathway of the salty sweat glands. The first two mechanisms require further diffusion through the rest of the epidermis and dermis. The third mechanism allows diffusional leakage into the epidermis and direct permeation into the dermis.

Transdermal delivery of drugs has attributes that make it far superior to other modes of systemic drug administration. Despite these advantages, relatively few drugs are deliverable transdermally. The majority of drugs will not penetrate the skin at rates sufficiently high for therapeutic efficacy.

In vitro steady state fluxes of a drug through the skin have ranged as low as 0.00013 microg/$cm^2$ hr digitoxin to 300 microg/$cm^2$ hr for ephadrine. Several factors on the nature of skin must be considered in determining the degree of transdermal permeation. For example, the type of skin which the substance is to pass through varies from species to species, varies according to age, with the skin of an infant having a greater permeability than that of an older adult, varies according to local composition, thickness and density, varies as a function of injury or exposure to agents such as organic solvents or surfactants, and varies as a function of some diseases such as psoriasis or abrasion. In order to allow clinically useful transdermal application of drugs, some way to enhance and control their rates of penetration must be found.

It is therefore an object of the invention to provide a method for enhancing and controlling permeation of a molecule through the skin and into the circulatory system.

It is a further object of the invention to provide a method for enhancing permeation which operates externally to the skin and does not harm either the skin or the molecules being infused.

It is still another object of the invention to provide an improved method for transdermal delivery of drugs where the primary goal is to achieve a suitable therapeutic blood level.

It is a further object of the present invention to provide an improved method for transdermal delivery of a drug which is useful with a variety of molecules, including molecules soluble in an aqueous, inorganic or lipid solution.

It is another object of the invention to provide a versatile method which is useful with both viable and non-viable skin.

It is still another object of the present invention to provide a simple, efficient, reproducible and economical method for enhancing transdermal permeation.

SUMMARY OF THE INVENTION

The present invention is a method using ultrasound for enhancing and controlling transdermal permeation of a molecule, including drugs, antigens, vitamins, inorganic and organic compounds, and various combinations of these substances, through the skin and into the circulatory system. The frequency and intensity of ultrasonic energy which is applied, the media between the ultrasonic applicator and the skin, and the length of time of exposure are determined according to the type of skin and the substance to be diffused transdermally. Levels of the diffused molecules in the blood and urine measured over a period of time are initially used to determine under what conditions adequate transfer occurs.

In general, the frequency range of the ultrasound is between 20 kHz and 10 MHz, with intensities between 0 and 3 W/cm$^2$. Intensity is decreased as the frequency is decreased to prevent damage to the skin. The preferred range of frequencies is between 0.5 MHz and 1.5 MHz and the preferred range of intensities is between 2 and 4 W/cm$^2$. Exposure is for between 1 and 10 minutes for most medical uses. The ultrasound may be pulsed or continuous. However, the frequency, intensity and time of exposure are interdependent as well as a function of the molecule being diffused and the nature of the skin at the site of exposure. One way of determining the maximum limit of exposure is to measure skin temperature, decreasing or stopping the treatment when the temperature of the skin rises one to two degrees Centigrade.

In an alternate embodiment of the invention, ultrasonic energy is used to enhance passage of other molecules into and through non-living skin, for example, to increase the rate of diffusion of preservatives or dyes into animal hides or fine furs.

Enhancement of both in vivo and in vitro transdermal transfer is shown by examples of the permeation of radiolabelled $^3$H-D-mannitol and $^3$H-inulin through the skin of rats and mice. A test solution of 5–20 microl. $^3$H-D-mannitol was applied to the back skin of hairless mice and to a shaven site on the upper back of the rats, followed by an aquasonic gel.

Radioactive excretion after topical application of 20 microl. of $^3$H-D-mannitol, followed immediately by ultrasound application at 1.5–2.0 W/cm$^2$ for 2–3 minutes, showed that ultrasound treated rats had 20 times more radioactivity in the urine secreted during the first two hours than did the controls.

DETAILED DESCRIPTION OF THE INVENTION

The present invention is a method for enhancing the rate and efficacy of permeation of a drug into and through skin into the circulatory system which utilizes a limited exposure of the skin to ultrasound. The ultrasound alters the passage of the molecules through the stratum corneum, via inter-cellular, intra-cellular, and transappendageal penetration. The required length of time and frequency and intensity of ultrasound exposure are dependent on a number of factors including skin thickness and resistance to permeation which varies from species to species, with age, injury or disease, and by location on the body.

Ultrasound is sound having a frequency greater than 20 kHz. Ultrasound used for medical diagnostic purposes usually employs frequencies ranging from 1.6 to about 10 MHz. As disclosed here, frequencies of between 20 kHz and 10 MHz with intensities between 0 and 3 W/cm$^2$, preferably between 2 and 4 W/cm$^2$, are used to enhance transdermal transfer of molecules. The preferred frequency range is between 0.5 MHz and 1.5 W/cm$^2$. Devices are available which emit both pulsed and continuous ultrasound. Exposures of only a few minutes are usually sufficient since the response time to the ultrasound is very rapid. Care must be taken to avoid excessive exposure which might cause burning. The temperature of the skin is one indicator of overexposure. In the present invention, the temperature is held under 38° C. for human skin.

In the examples given below, rat and mouse skin is treated in vivo with 1 to 2 W/cm$^2$ ultrasound energy at a frequency of 870 kHz for one to three minutes. Rat and mouse skin is treated in vitro at lower frequencies, in the range of 75 kHz, for longer periods, up to two hours. Maximum effect of the ultrasound is achieved by applying it immediately after topical application. Little effect is noted if the ultrasound is applied more than ten hours after topical application of the drug.

The specific embodiment of the ultrasound device is not important. Probes, baths and boxes are all useful depending on where the ultrasound is to be applied. A number of devices are commercially available. It is possible that an ultrasound applicator analogous to the high pressure devices commonly used for mass vaccinations could be developed for rapid, easy, repeated treatment of patients transdermally.

Ultrasound does not transmit well in air so a liquid media between the ultrasound applicator and the skin is preferred. Any type of aqueous or inorganic gel may be used, including one of the many commercially available products. Preferably, the medium should have an absorption coefficient similar to that of water. Alternatively, the applicator may be applied directly to a "patch" containing the molecules to be transdermally transferred, such as the drug patches presently in use for transdermal drug transfer without ultrasound. These patches generally consist of a protective cover, a matrix containing the drug, a support, and adhesive to hold the patch in place.

The advantage of using ultrasound is that the rate and efficiency of transfer is improved. Drugs which would simply not pass through the skin and into the circulatory system are forced through the skin when ultrasound is applied. By controlling the frequency, intensity and time of exposure, the rate of transfer is controlled. Measurements taken over time of the blood or urine concentrations can be used to determine at what point the ultrasound conditions are correct.

In the preferred embodiment, ultrasound is used to enhance the passage of a compound such as a large molecular weight or polar molecule through the skin of a patient. Greater control and drug utilization is achieved by increasing the rate and directional control of the applied drug. The percentage of drug which quickly enters the bloodstream is increased accordingly and undesirable side effects avoided. The application of ultrasound allows transdermal infusion of drugs which would otherwise not be possible. The goal is to transdermally infuse molecules into the bloodstream at an optimal rate. In the transdermal devices or "patches" presently in use, even drugs with low molecular weights such as nitroglycerin take 30 minutes to enter the bloodstream. A hypertension drug such as Catapresan may take up to two days to fully enter the bloodstream. It is highly desirable to decrease the rate of entry of these drugs to a matter of a few minutes, approximately the time required for the drug to enter the bloodstream when given orally.

The safety and efficacy of the disclosed method was demonstrated by the following non-limiting example employing $^3$H-labelled Mannitol and Inulin.

These compounds were selected since D-mannitol, a highly polar sugar alcohol, and inulin, a large molecular weight polysaccharide, m.w. 5200, are poor skin penetrants, thus enabling detection of minor permeation changes, and both D-mannitol and inulin are totally and rapidly excreted, permitting direct in vivo monitoring of the amount of the drug in the blood stream.

EXAMPLE 1

In Vitro Enhancement of Skin Permeability

Skin permeability changes caused by ultrasound energy were determined by an in vitro diffusion procedure using double chamber cells. The diffusion cells were composed of two separate compartments (4.5 and 5.5 ml) designed to be clamped together across a 1.3 cm diameter opening in the side of each compartment. Magnetic stirring bars in each chamber were used for mixing. Animals were sacrificed using $CO_2$, and a piece of the dorsal skin removed. Skin specimens were held between the cells with a pressure clamp, the stratum corneum facing the donor solution. The donor compartment contained 20 microCi D-$^3$H-mannitol in a saturated solution of D-mannitol in buffered saline solution containing an 0.1M phosphate at pH 7.3. The receiver solution was buffered saline. The cells were placed in the center of a water-filled ultrasonic bath, RAI Research Corporation Model 250, which generated an ultrasonic frequency of 75 kHz in a thermostated stainless steel tank of 3.5"×3.5"×2.5". Permeability experiments were performed within the first two hours of switching in the ultrasound. 200 microliter samples were withdrawn from the receiver solution over time, and replaced with 200 microliters of buffered saline. The radioactivity of the withdrawn samples was measured by liquid scintillation counting. All experiments were conducted at room temperature, 22° C. No ultrasound was applied on the controls.

Figure 2:
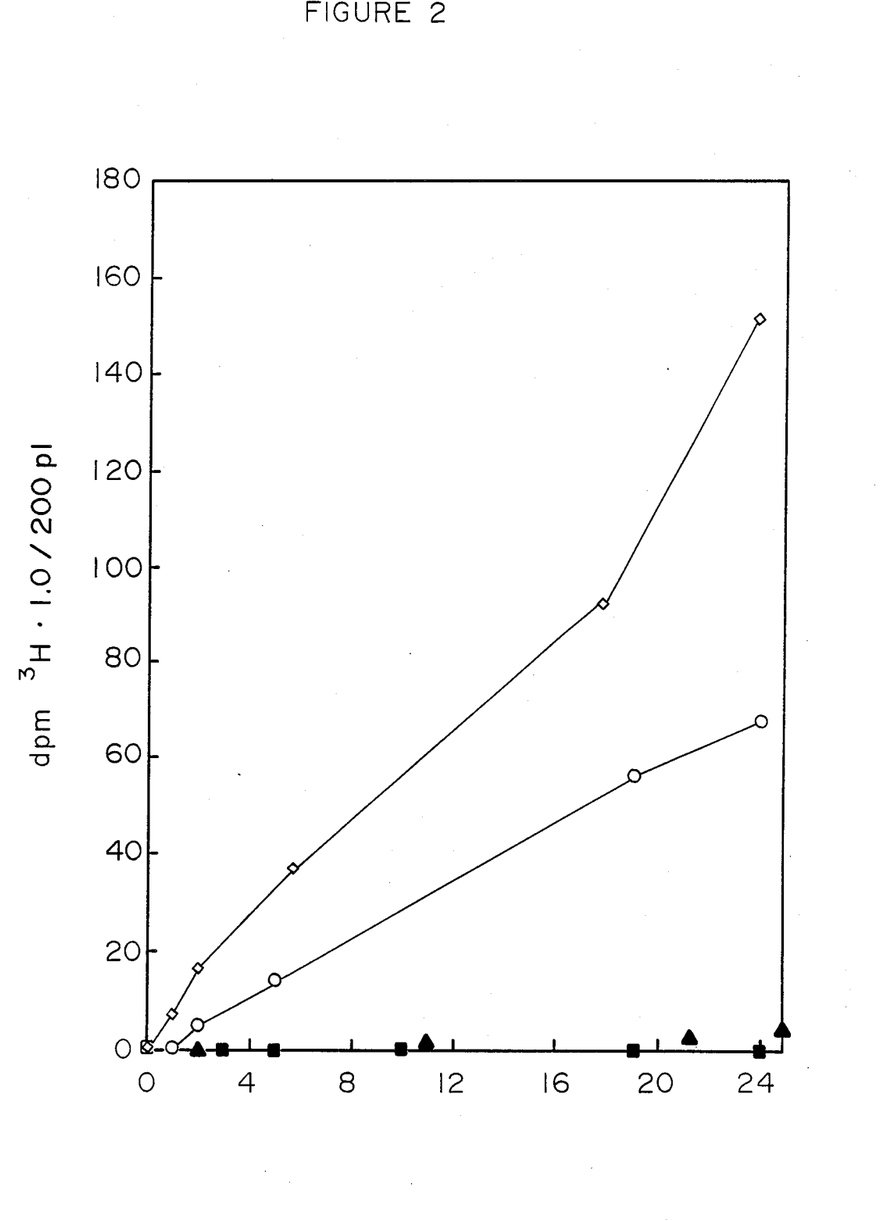
FIG. 2 is a graph of the diffusion of $^3$H-D-Mannitol through the skin of rats with ◇–◇ and without ◆–◆ ultrasound, and mice, with –⊖–⊖– and without –●–●– ultrasound.

Two hours of ultrasound irradiation at 75 kHz of cells containing $^3$H-D-Mannitol solution diffusing through the skin of rats and mice in vitro caused a 50 to 80% increase in drug permeation, as shown in FIG. 2. The same effect was observed when the skin was irradiated for two hours before the drug was introduced into the donor cell.

Ultrasound irradiation did not damage mouse skin permeability. However, SEM studies show a higher degree of mechanical surface rupture in the in vitro mouse skin irradiated for 2 hours at 75 kHz and relatively high intensity, as compared to a control skin or to mouse skin irradiated in vivo for 1 min. at 870 kHz, 1.5 W/cm$^2$.

EXAMPLE 2

In Vivo Enhancement of Skin Permeability

The effect of ultrasound energy on skin penetration of D-$^3$H-mannitol and $^3$H-inulin in rats and mice in vivo was determined.

Sprague-Doweley (CD) male rats (weighing 200-250 g each) and hairless mice were used in this example. The conditions were chosen so as to minimize external skin damage. An ultrasonic therapy unit, Burdick UT420A, approved for use in the treatment of human and animal tissue to facilitate healing through a combination of mechanical and thermal effects, was used for the in vivo studies.

Test solutions of 5 to 20 microliter D-$^3$H-mannitol were applied to a shaven site in the upper back of the rats, followed by an aquasonic gel. Surface changes in skin from both in vivo and in vitro experiments were investigated by electromicroscopy technique. For scanning electron microscopy (SEM) examination, pieces of dorsal skin from the mice and rats were fixed with 2% glutaraldehyde, followed by 1% osmium tetroxide, dehydrated in a series of ascending alcohol concentrations, followed by critical point drying and examined with the electron microscope.

Measurement of the amount of drug excreted in the urine was determinative of the rate of permeation in in vivo studies. Urine was collected via a catheter inserted into the bladder. The incision was stitched closed and the rat put in a restrainer. Test solutions of microl. $^3$H-D-mannitol and 12.5-50 microl. $^3$H-inulin were applied to the skin, followed by ultrasound application. Urine was collected every 15-30 minutes for the first 2 hours and at several time points afterwards. Volume and radioactivity of each urine sample was measured.

Urine samples of ultrasound treated and control rats were compared by thin layer chromatography on silica plates developed in t-butanol:pyridine:water (6:4:3) visualized by phosphomolybdic acid reagent. The developed silica gel plate was cut into several sections according to the distance migrated by the spots relative to each other ($R_f$) and the pieces placed in scintillation vials. One milliliter of distilled water was added to each vial to dissolve the drug. 10 ml of Aquasol TM (New England Nuclear, Boston, MA) scintillation liquid was added, and the radioactivity measured.

Figure 3:
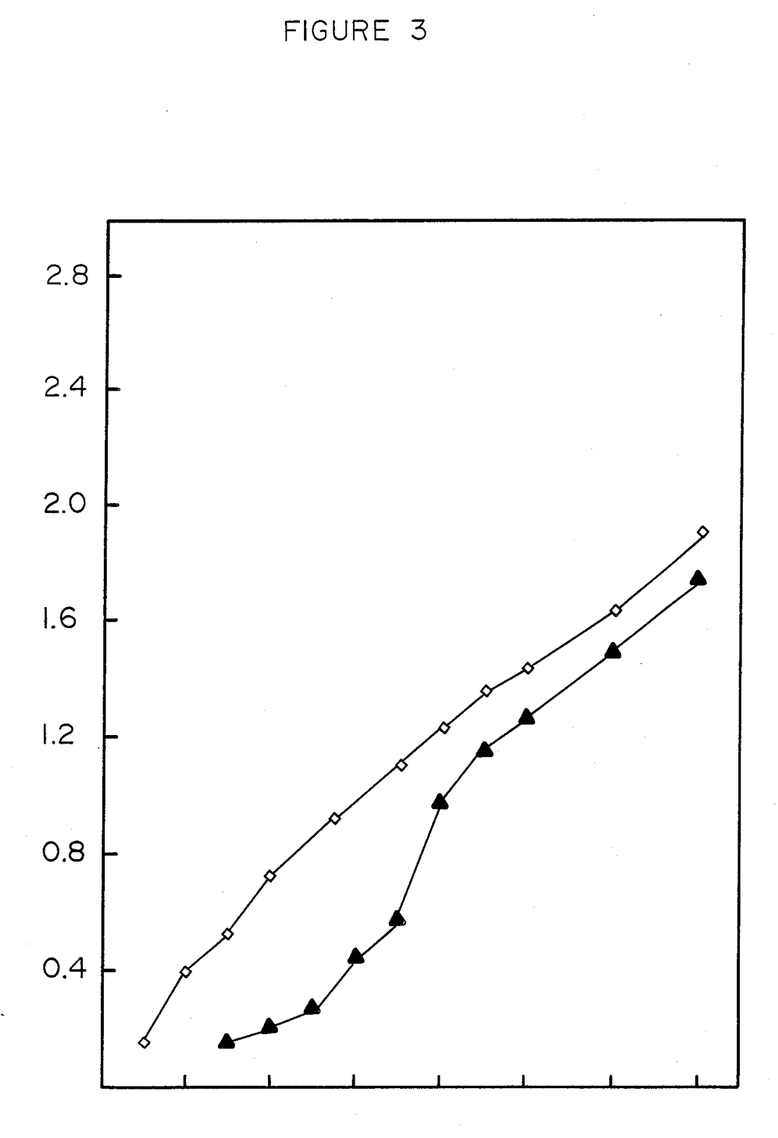
FIG. 3 is a graph of the excretion of [$^3$H]-D-Mannitol in the urine of rats after topical application of 20 microCi [$^3$H]-D-Mannitol with ◇–◇ or without ▲–▲ ultrasound.

FIG. 3 compares excretion of $^3$H-D-mannitol after topical application of 20 microliter radiolabeled $^3$H-D-mannitol, followed immediately by ultrasound treatment at 1.5-2.0 W/cm$^2$ for 2-3 minutes, with excretion by control rats (no ultrasound). The ultrasound treated rats had 20 times more radioactivity in their urine during the first two hours than did the control rats. The effect of the ultrasound decreased with time. After 10 hours the radioactivity in the urine of the two groups was indistinguishable. The difference in release rate of $^3$H-D-mannitol was observed only if the ultrasound treatment was applied immediately after drug application. When the rats were treated with ultrasound, 10 or more hours after drug application, no change in the release rate was observed.

Mannitol is totally and rapidly eliminated from the body and therefore appears completely in the urine. The effect of ultrasound on the permeating molecules as evaluated by thin layer chromatography indicated no decomposition of the mannitol by the ultrasonic energy.

Figure 4A:
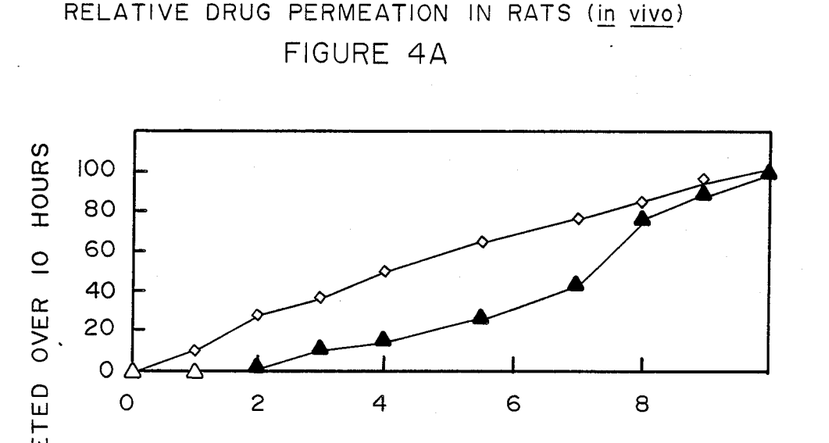
FIG. 4a–c are graphs of the percentage of $^3$H-drug excreted in the urine of rats over a period of ten hours after topical application of (a) 20 micro Ci [$^3$H]-D-Mannitol, (b) 10 microCi [$^3$H]-D-Mannitol, and (c) 50 microCi [$^3$H]-Inulin, with ◇–◇ or without ▲–▲ ultrasound.
Figure 4B:
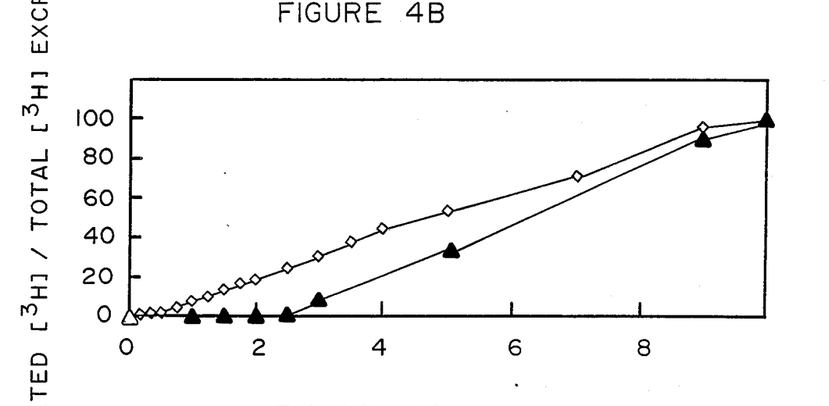
Figure 4C:
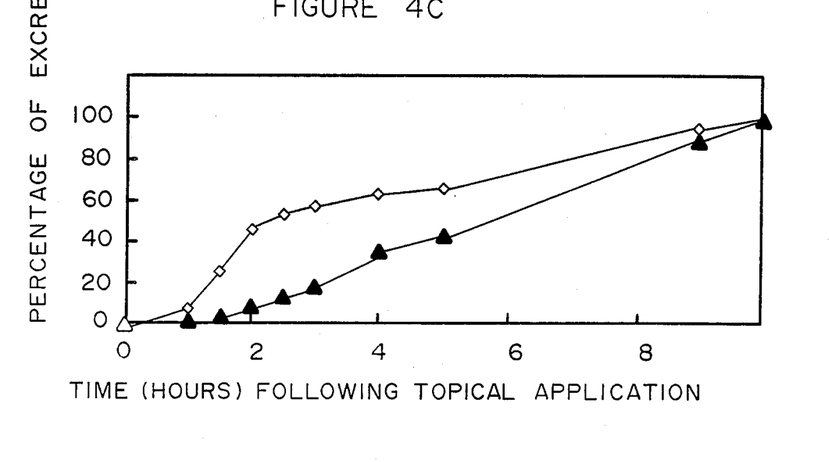

FIG. 4 compares the percentage of excreted [$^3$H] at a specific time interval to total amount of radioactivity excreted over 10 hours following topical application of both $^3$H-D-mannitol and $^3$H-inulin in rats. This was used as a measure of the relative drug penetration. In the ultrasound treated rats the percentages of [$^3$H] excreted during the first two hours were 20% to 30% for $^3$H-D-mannitol and 50% for $^3$H-inulin as compared to 2-5% for $^3$H-D-mannitol and 10% for $^3$H-inulin in the respective controls. As shown by Table I, the ratio of relative drug permeation, R, is defined as:

$$R(t) = \frac{p_{us}(t)}{p_{ct}(t)}$$

where $p_{us}$ is the percentage of [$^3$H] in urine of ultrasound treated rats at a time, t, divided by the total amount of [$^3$H] excreted in the urine over 10 hours. $p_{ct}$ is the percentage of [$^3$H] in the urine of untreated rats at a time, t, divided by the total amount of [$^3$H] excreted by the rats over a period of ten hours. As can be seen from Table I, skin permeation for both drugs was 6 to 20 fold greater in ultrasound treated rats during the first 2 hours than that of the corresponding control group.

TABLE I

| time (hours) | Ratio of relative drug permeation in rats | | |
|---|---|---|---|
| | D-$^3$H—mannitol | | $^3$H—inulin |
| | 20 mCi | 10 mCi | 50 mCi |
| 2 | 19 | 19 | 6 |
| 5 | 2.5 | 1.5 | 1.5 |
| 10 | 1 | 1 | 1 |

Figure 5:
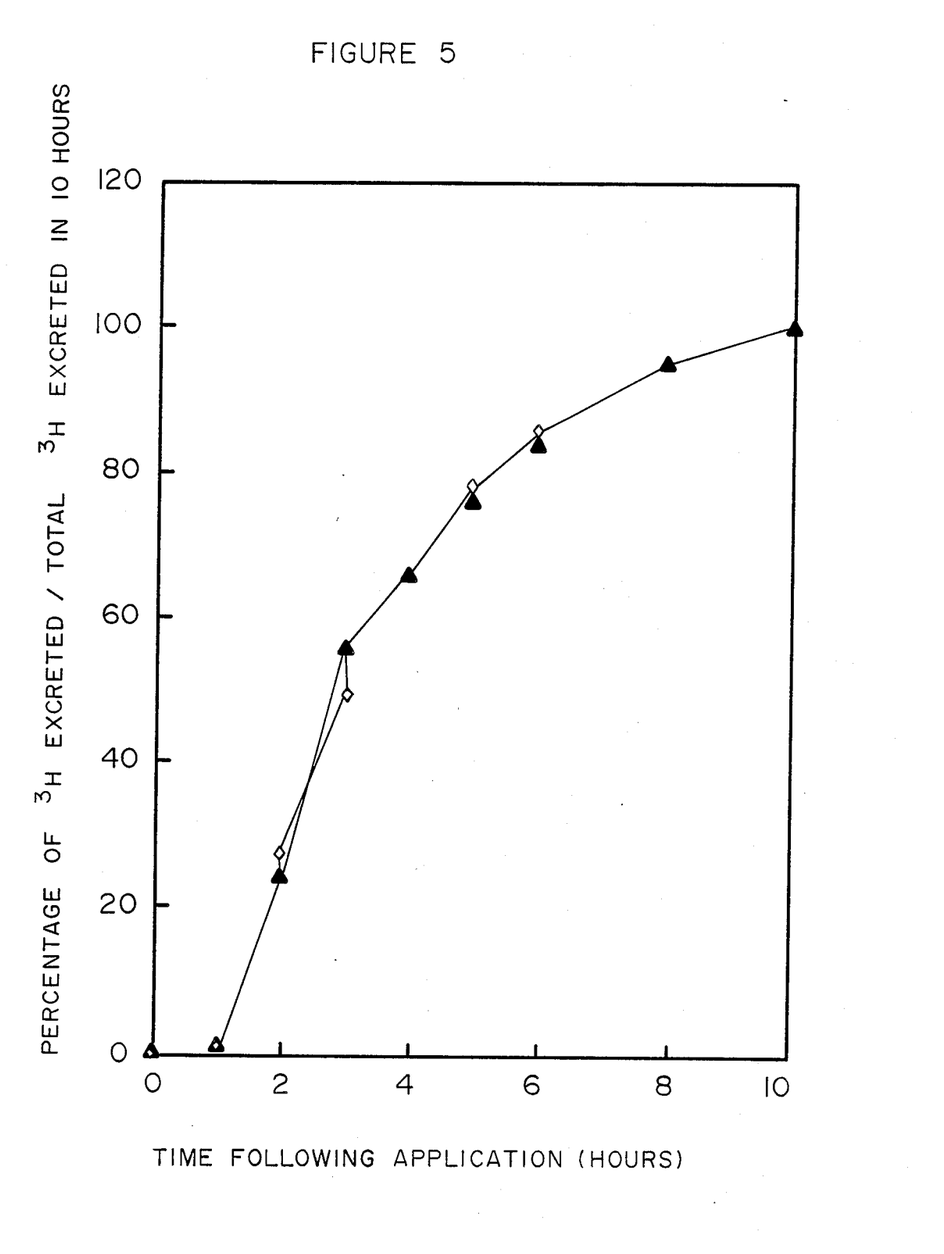
FIG. 5 is a graph of the percentage of [$^3$H]-D-Mannitol excreted in the urine of hairless mice over a period of ten hours after topical application of 5 microCi with ◇–◇ and without ▲–▲ ultrasound.

FIG. 5 shows the relative D-mannitol permeation in mice after the application of 5 microl. $^3$H-D-mannitol followed immediately by ultrasound treatment at 1-1.5 W/cm$^2$ for 1 min. The results are expressed as the percentage of [$^3$H] excreted at a specified time divided by the total [3H] excreted over ten hours.

There was no change in the percentage of excreted radioactivity when the ultrasound treatment was applied 10 hours after drug application.

These examples demonstrate that the transdermal permeation of $^3$H-D-mannitol and $^3$H-inulin in rats is increased 6-20 fold within the first two hours of ultrasound treatment. This increase was observed only during the initial phase of the transdermal permeation, before establishment of a steady state. The fact that the ultrasound energy shortened the lag time for transdermal permeation of D-mannitol and inulin in rats, and did not change the drug release rate during the steady-state phase, suggests that the ultrasound treatment enhanced the diffusion of the administered drugs through an alternative pathway such as the hair follicles in the rat's skin, rather than diffusion through the bulk of the stratum coreum.

Intensities of less than 5 W/cm$^2$ of ultrasound at a frequency of 1 MHz do not result in a significant temperature rise nor have any destructive effect on viable mouse or rat skin. Skin temperature did not increase more than 1° C. when ultrasound energy was applied for less than 3 minutes to rats at less than 3 W/cm$^2$ or 1 minute to mice at 1.5 W/cm$^2$. Longer treatment sometimes caused skin burns.

In summary, the examples using skin from two species, both in vivo and in vitro, demonstrate that ultrasound is an effective means of enhancing the passage of molecules through skin and into the circulatory system. Frequencies, power and time of application can be optimized to suit the individual situation, both with respect to the type of skin and the molecules to be diffused.

Although this invention has been described with reference to specific embodiments, it is understood that modifications and variations of the method for using ultrasound energy to enhance passage of molecules into and through skin may occur to those skilled in the art. It is intended that all such modifications and variations be included within the scope of the appended claims.

We claim:

1. A method for enhancing and controlling transdermal infusion of molecules comprising:
   (a) selecting the molecules having a low rate of permeability through the skin to be infused;
   (b) applying to the skin said molecules in a medium with an absorption coefficient similar to that of water;
   (c) applying ultrasound to said molecules in said medium at a frequency of between 20 kHz and 10 MHz and an intensity of between 0 and 3 W/cm$^2$; and
   (d) varying the frequency and intensity over time to transdermally infuse said molecules at an optimal rate into the circulatory system without delay or damaging the skin, wherein the optimal rate is determined by measurements of a physiological fluid.

2. This method of claim 1 wherein the ultrasound frequency is applied at between 0.5 MHz and 1.5 MHz and an intensity of between 2 and 4 W/cm$^2$.

3. The method of claim 1 wherein the ultrasound is applied for less than 10 minutes.

4. The method of claim 1 further comprising suspending the molecules to be applied in an aqueous gel.

5. The method of claim 1 further comprising constructing a transdermal drug patch formed of a support, adhesive, a drug-containing matrix and a protective covering for applying the molecules to the skin.

6. The method of claim 1 wherein the ultrasound is applied continuously.

7. The method of claim 1 wherein the ultrasound is pulsed.

8. The method of claim 1 further comprising selecting said molecule from the group of molecules consisting of proteins, drugs, antigens, vitamins, inorganic compounds, organic compounds, and combinations thereof, wherein said molecule has a biological effect when infused into the circulatory system.

9. The method of claim 1 further comprising measuring the temperaure of the skin where the ultrasound is applied.

10. The method of claim 9 wherein the ultrasound is applied at a frequency and intensity over a period of time which does not cause an increase in skin temperature of more than 2° C.

11. The method of claim 1 further comprising measuring the concentration of said molecules in a physiological fluid during or immediately after administration of the ultrasound.

12. The method of claim 1 further comprising measuring the concentrations of said molecule in the physiological fluid over time, determining the rate of transdermal transfer for said molecules at specific frequencies, intensities and times of ultrasound application, wherein the molecules are subsequently infused using ultrasound at the frequency, intensity and time of application determined to yield a specific concentration.

* * * * *

UNITED STATES PATENT AND TRADEMARK OFFICE
CERTIFICATE OF CORRECTION

PATENT NO. : 4,767,402

DATED : August 30, 1988

INVENTOR(S) : Joseph Kost et al.

It is certified that error appears in the above-identified patent and that said Letters Patent is hereby corrected as shown below:

Column 6, line 48, the number "10" should be inserted after the word "of".

Signed and Sealed this

Twenty-first Day of February, 1989

Attest:

DONALD J. QUIGG

Attesting Officer

Commissioner of Patents and Trademarks